(12) United States Patent
von Ilberg et al.

(10) Patent No.: US 9,802,043 B2
(45) Date of Patent: Oct. 31, 2017

(54) INDUCTIVE SIGNAL AND ENERGY TRANSFER THROUGH THE EXTERNAL AUDITORY CANAL

(75) Inventors: Christoph von Ilberg, Kronberg/Ts (DE); Dominik Hammerer, Innsbruck (AT); Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1188 days.

(21) Appl. No.: 12/957,550

(22) Filed: Dec. 1, 2010

(65) Prior Publication Data
US 2011/0130622 A1 Jun. 2, 2011

Related U.S. Application Data

(60) Provisional application No. 61/265,399, filed on Dec. 1, 2009.

(51) Int. Cl.
*H04R 25/00* (2006.01)
*A61N 1/36* (2006.01)
(Continued)

(52) U.S. Cl.
CPC ..... *A61N 1/36032* (2013.01); *A61N 1/37229* (2013.01); *A61N 1/08* (2013.01); *H04R 25/606* (2013.01)

(58) Field of Classification Search
CPC .............. A61N 1/36032; A61N 1/0541; A61N 1/3787; A61N 1/37229; A61N 1/37217; A61N 1/0526; A61N 1/05; H04R 25/606; H04R 25/554; H04R 2225/67; H04R 25/00; H04R 25/55; H04R 2225/51;
(Continued)

(56) References Cited

U.S. PATENT DOCUMENTS

| 4,352,960 A | 10/1982 | Dormer et al. ................ 179/107 |
| 4,696,287 A | 9/1987 | Hortmann et al. ........... 128/1 R |

(Continued)

FOREIGN PATENT DOCUMENTS

| DE | 102004050616 B3 | 3/2006 | ............. H04R 25/00 |
| EP | 0 259 906 A2 | 3/1988 | ............... A61F 2/02 |

(Continued)

OTHER PUBLICATIONS

International Search Report and Written Opinion, PCT/US2010/058481, dated Jul. 6, 2011.

*Primary Examiner* — Deborah Malamud
(74) *Attorney, Agent, or Firm* — Sunstein Kann Murphy & Timbers LLP

(57) ABSTRACT

An inductive coil arrangement is described for an ear canal of a recipient patient. An inner transmitter coil inserts into the ear canal for transmitting a communication signal through the skin of the outer wall of the ear canal. The transmitter coil includes transmission wire loops that lie substantially in a common plane which curves around the central axis of the ear canal conformal to the outer wall of the ear canal. An outer receiver coil is implantable under the skin of the outer wall of the ear canal for receiving the communication signal from the transmitter coil. The receiver coil includes receiver wire loops that lie substantially in a common plane which curves around the central axis of the ear canal substantially parallel to the transmitter coil.

14 Claims, 5 Drawing Sheets

(51) Int. Cl.
*A61N 1/372* (2006.01)
*A61N 1/08* (2006.01)

(58) Field of Classification Search
CPC  H04R 25/60; H04R 2225/025; H04B 5/0081;
H04B 5/0093; H04B 5/0031; H04B
5/0037; H04B 5/06; A61B 5/0031; A61M
2210/0668; A61M 2039/0267; A61M
2210/0662; H02J 7/025; H02J 5/005;
H01R 2201/12
USPC ......... 381/312–313, 322, 328, 331; 607/1–2,
607/55–57, 115–116, 136–137
See application file for complete search history.

(56) References Cited

U.S. PATENT DOCUMENTS

| | | | |
|---|---|---|---|
| 4,932,405 A | 6/1990 | Peeters et al. | 607/57 |
| 5,558,618 A | 9/1996 | Maniglia | 600/25 |
| 6,556,870 B2 | 4/2003 | Zierhofer et al. | 607/57 |
| 7,139,404 B2 * | 11/2006 | Feeley et al. | 381/330 |
| 2004/0093040 A1 | 5/2004 | Boylston et al. | 607/57 |
| 2006/0030905 A1 | 2/2006 | Medina Malaver | 607/61 |

FOREIGN PATENT DOCUMENTS

| | | | | |
|---|---|---|---|---|
| WO | WO 98/09588 | 3/1998 | | A61F 11/04 |
| WO | WO 2010/133702 A2 | 11/2010 | | A61M 11/04 |

* cited by examiner

US 9,802,043 B2

INDUCTIVE SIGNAL AND ENERGY TRANSFER THROUGH THE EXTERNAL AUDITORY CANAL

This application claims priority from U.S. Provisional Patent Application 61/265,399, filed Dec. 1, 2009, which is incorporated herein by reference.

FIELD OF THE INVENTION

The present invention relates to implantable medical devices, and more specifically to an inductive coil arrangement for such devices.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. In response to received sounds transmitted by the middle ear 103, the fluid filled cochlea 104 functions as a transducer to generate electric pulses that are transmitted to the acoustic nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that stimulates auditory nerve tissue with electrical stimulation signals delivered by multiple electrode contacts distributed along an implant electrode. FIG. 1 shows some components of a typical cochlear implant system where an external microphone provides an audio signal input to an external signal processing stage 111 that implements one of various known signal processing schemes. The processed signal is converted by the external signal processing stage 111 into a digital data format communication signal for transmission by a transmitter coil 107 into an implanted receiver stimulator 108. Besides extracting the audio information, the receiver stimulator 108 may perform additional signal processing such as error correction, pulse formation, etc., and produces a stimulation pattern (based on the extracted audio information) that is sent through electrode wires 109 to an implant electrode 110. Typically, the implant electrode 110 includes multiple electrodes on its surface that provide selective stimulation of the cochlea 104.

Hearing systems such as those described above are known to have various difficulties associated with the transmitter coil 107. For example, in the arrangement described above, the transmitter coil 107 and the receiver stimulator 108 include permanent magnets used to hold the transmitter coil 107 in correct position over the receiver stimulator 108. These magnets create problems with magnetic resonance imaging (MRI) or at the skin which covers the receiver stimulator 108. In addition, the location of the transmitter coil 107 on the head behind the outer ear 101 leaves it exposed to impact (e.g., during sports) or being accidentally wiped or brushed off (e.g., while brushing the hair).

U.S. Pat. No. 4,696,287 by Hortmann et al. disclosed a coil system for an implanted hearing aid where the external transmitter coil was located in the ear canal with its windings wrapped perpendicular to the axis of the ear canal, and where the implanted receiver coil was a ring surrounding the ear canal. U.S. Pat. No. 7,120,501 by Boylston et al. disclosed a hearing implant system which included a transmitter coil in the ear canal and a receiver coil positioned in the middle ear on the other side of the ear drum from the transmitter coil. Both of the above systems required that the implanted receiver coil have wire windings concentrated at certain specific radii and no uniform winding from the center to an outer radius was possible. WO 9809588 by Seligman et al. disclosed a coil arrangement with one coil in the outer ear canal and another implanted beside the ear canal, where each coil included two orthogonally wound sub-coils around a ferrite core.

SUMMARY OF THE INVENTION

Embodiments of the present invention are directed to an inductive coil arrangement for the ear canal of a recipient patient. An inner transmitter coil is inserted into the ear canal for transmitting a communication signal through the skin of the outer wall of the ear canal. The transmitter coil includes transmission wire loops that lie in a common plane which curves around the central axis of the ear canal conformal to the outer wall of the ear canal. An outer receiver coil is implanted under the skin of the outer wall of the ear canal for receiving the communication signal from the transmitter coil. The receiver coil includes receiver wire loops that lie substantially in a common plane which curves around the central axis of the ear canal substantially parallel to the transmitter coil.

The coils may curve partially around the circumference of the ear canal in a C-shape, or completely around the circumference of the ear canal. An innermost end of the transmitter coil nearest the tympanic membrane may include a sealing edge that folds back when the transmitter coil is inserted into the ear canal. The transmitter coil may include a helical ridge for promoting a screwing insertion movement when the transmitter coil is inserted into the ear canal. The coils may be air coils without magnetic cores.

There also may be an encapsulation layer of biocompatible material covering at least one of the coils. The encapsulation layer may include a substance that inhibits production of cerumen (ear wax). The encapsulation layer also may have ventilation openings for ventilation of the underlying skin. The ventilation openings may have a uniform size and shape, or they may be different sizes.

In some embodiments, the transmission wire loops may be concentrated at one or more radii from a central axis of the transmitter coil. And some embodiments may also include an ear canal microphone attached to the inner transmitter coil for sensing sound present in the ear canal. Some embodiments may also further include a secondary external transmitter coil for positioning over the skin behind the ear of the patient to transmit a communication signal through the skin, and a secondary receiver coil for implantation under the skin behind the ear of the patient to receive the communication signal from the secondary external transmitter coil.

Embodiments of the present invention also include an inductive coil arrangement for a recipient patient. An external transmitter coil fits into the outer ear of the patient and transmits a communication signal through the skin of the outer ear. An implantable receiver coil is implantable under the skin of the outer ear between the pinna cartilage and the underlying skull bone for receiving the communication signal from the transmitter coil.

In further specific embodiments, the receiver coil lies in a plane under the pinna cartilage and atop and parallel to the underlying skull bone. there may also be an implantable connecting lead for connecting the receiver coil to an implanted stimulator to couple the communication signal to the implanted stimulator. An external processor may be connected to the transmitter coil for generating the communication signal.

Embodiments of the present invention also include an implantable medical device or system including an inductive coil arrangement according to any of the above.

DETAILED DESCRIPTION OF SPECIFIC EMBODIMENTS

Partially implantable systems such as hearing implants (HI) include both external and implantable components. Hearing implants include, e.g., cochlear implants (CI's), middle ear implants (MEI's), bone conduction implants, etc. In such systems, transfer of electrical energy and data signals is based on an external primary coil (referred to as the transmitter coil) and an internal secondary coil (referred to as the receiver coil). Many partially and totally implantable medical systems also require regular charging cycles for their implantable batteries. Instead of the traditional transcutaneous inductive link located on the side of the head near the mastoid bone above and behind the pinna (outer ear) as with existing HI systems, embodiments of the present invention transfer energy and data signals inductively through the skin at the outer wall of the ear canal.

Figure 1:
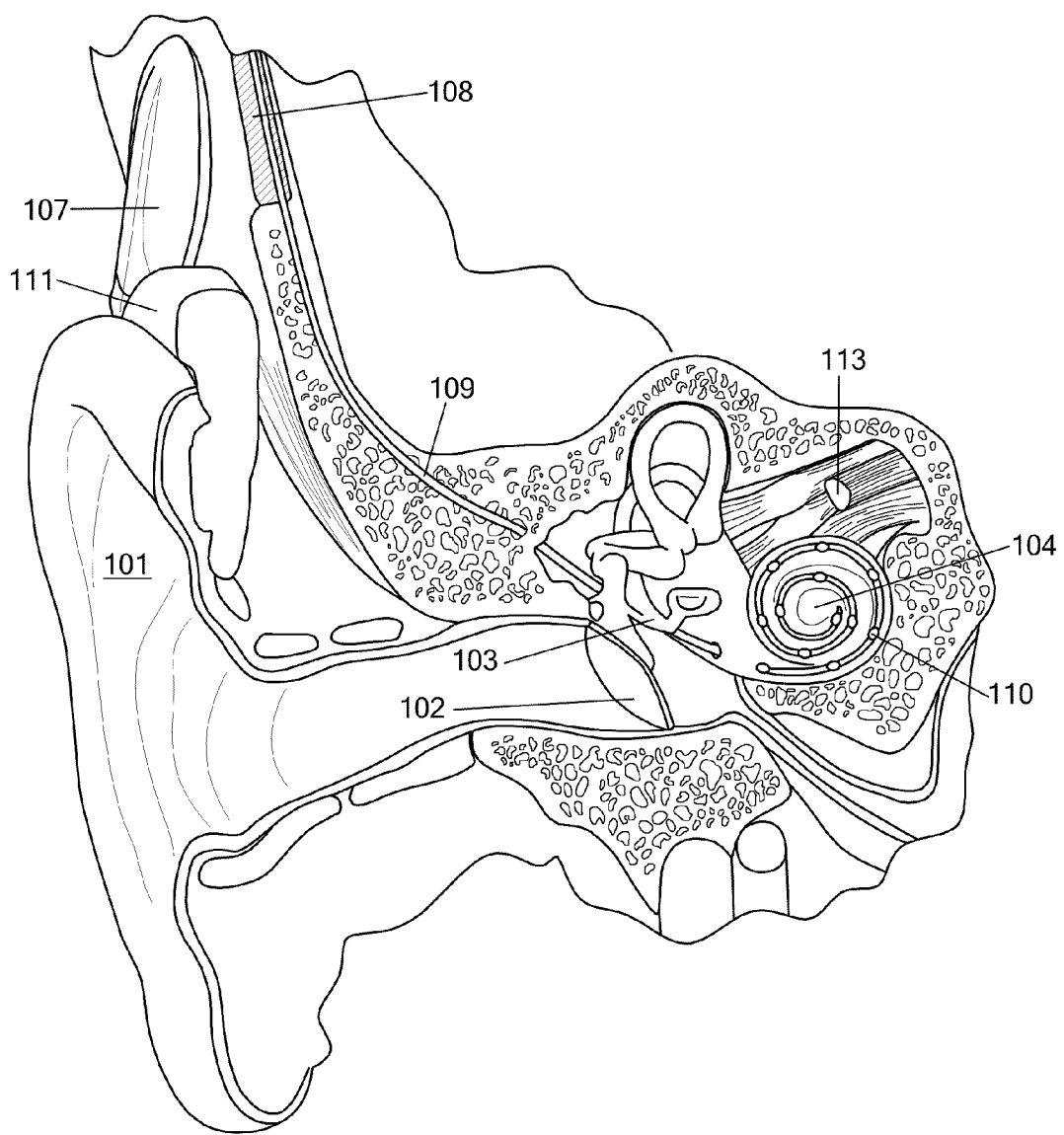
FIG. 1 shows elements of a human ear having a typical cochlear implant system.
Figure 2:
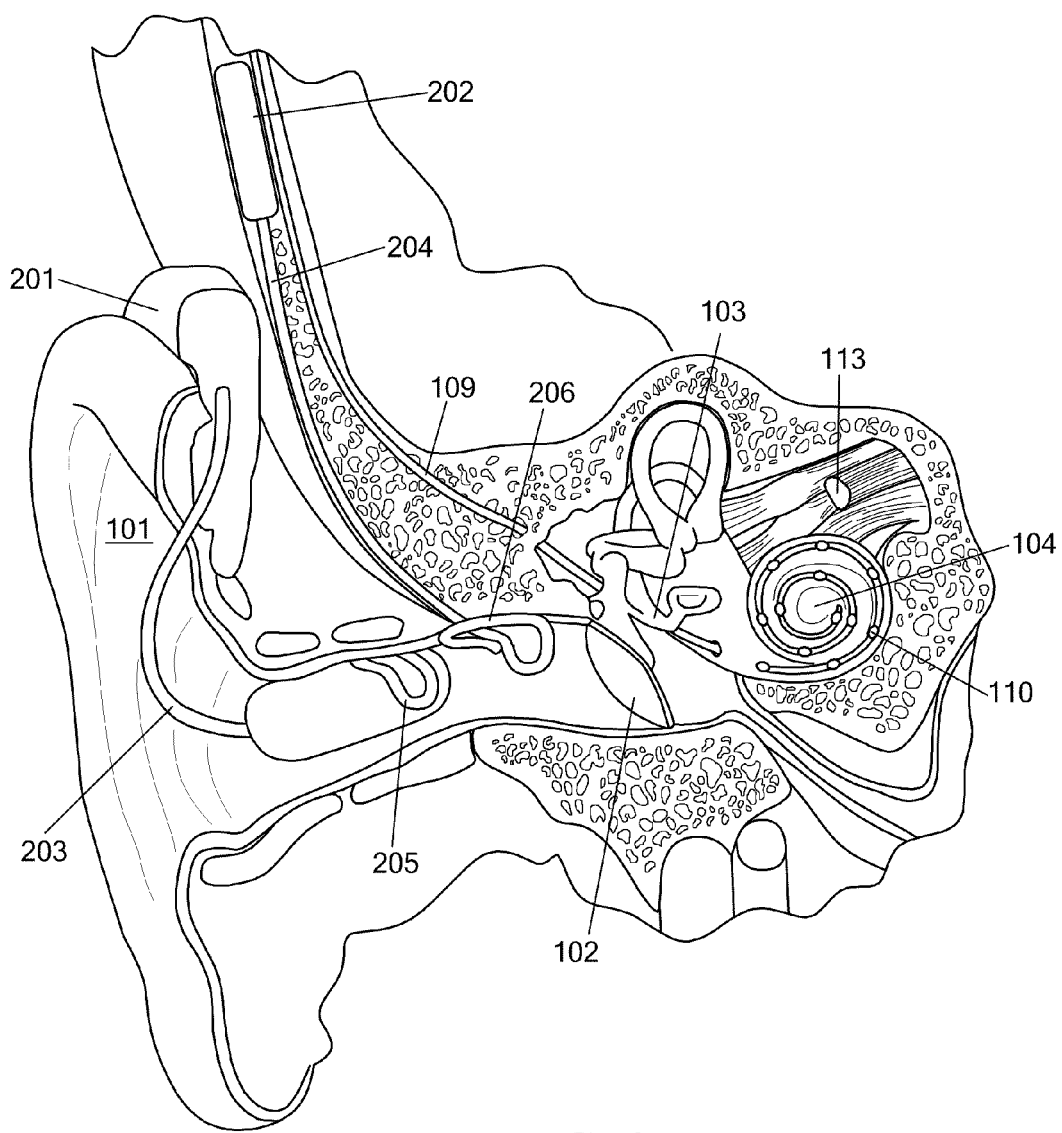
FIG. 2 shows an example of a coil arrangement according to one specific embodiment of the present invention.

FIG. 2 shows an inductive coil arrangement for an ear canal of a recipient patient according to one embodiment of the present invention. An inner transmitter coil 205 inserts into the ear canal 207. External processor 201 generates a communication signal providing energy and data components which coupling lead 203 provides to the transmitter coil 205. The coupling lead 203 may be stiff enough to help maintain the transmitter coil 205 in correct position in the ear canal 207. The transmitter coil 205 includes transmission wire loops that lie substantially in a common plane which curves around the central axis of the ear canal 207 conformal to the outer wall. The communication signal is transmitted by the transmitter coil 205 through the skin of the outer wall of the ear canal 207.

An outer receiver coil 206 is implantable under the skin of the outer wall of the ear canal 207 for receiving the communication signal from the transmitter coil 205. The receiver coil 206 includes receiver wire loops that lie substantially in a common plane which curves around the central axis of the ear canal 207 substantially parallel to the transmitter coil 205. Receiver lead 204 (e.g., around 30 mm long) couples the received communication signal from the receiver coil 206 to an implanted receiver stimulator 202 which then extracts the power and data components from the communication signal and generates an implant stimulation signal. For example, as shown in FIG. 2, the implanted receiver stimulator 202 provides the implant stimulation signal via electrode wires 109 to implant electrode 110 which includes stimulation electrodes 112 that stimulate neural tissue of the cochlea 104. The receiver coil 206 is relatively thin (e.g. based on a laminate arrangement), but relatively stiff such that it can easily fit between the skin covering the ear canal 207 and the underlying bone. Since (at least the outer part of) the ear canal 207 is flexible, the receiver coil 207 and its connected receiver lead 204 should be mechanically robust against small movements.

Figure 3:
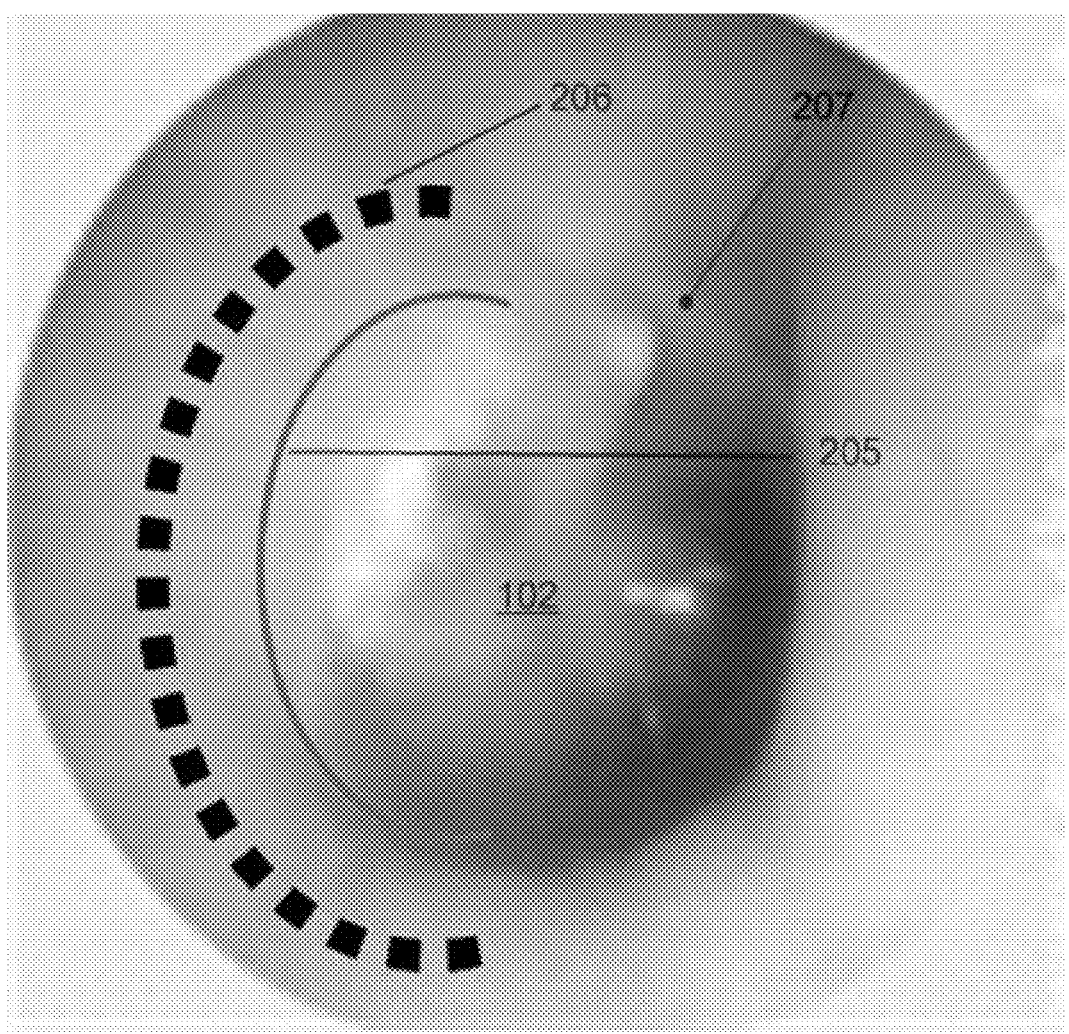
FIG. 3 illustrates placement of an embodiment with respect to the ear canal of a patient recipient.

Typically, the transmitter coil 205 and the receiver coil 206 are air coils without magnetic cores. The transmitter coil 205 and receiver coil 206 may curve as shown in FIG. 3 partially around the circumference of the ear canal 207 in a C-shape. In other embodiments, the coils may curve more or less completely around the circumference of the ear canal 207. In addition or alternatively, the transmitter coil 205 may include a helical ridge for promoting a screwing insertion movement when the transmitter coil 205 is inserted into the ear canal 207. Embodiments of an ear canal inductive coil system should be tolerant with regard to the relative position and orientation between the transmitter coil 205 and receiver coil 206, but the transmitter coil 206 still might benefit from a stable position to promote reliable and constant signal and energy transfer of the communication signal.

Figure 4B:
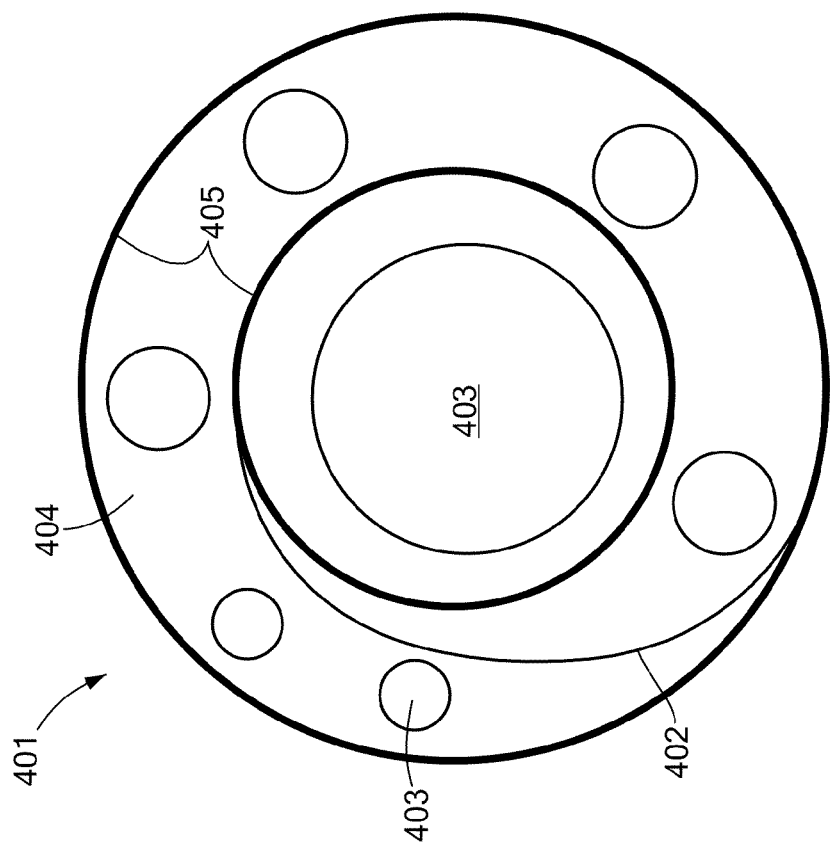
FIG. 4 A-B shows examples of an embodiment where the coils are embedded in a carrier having ventilation openings.
Figure 4A:
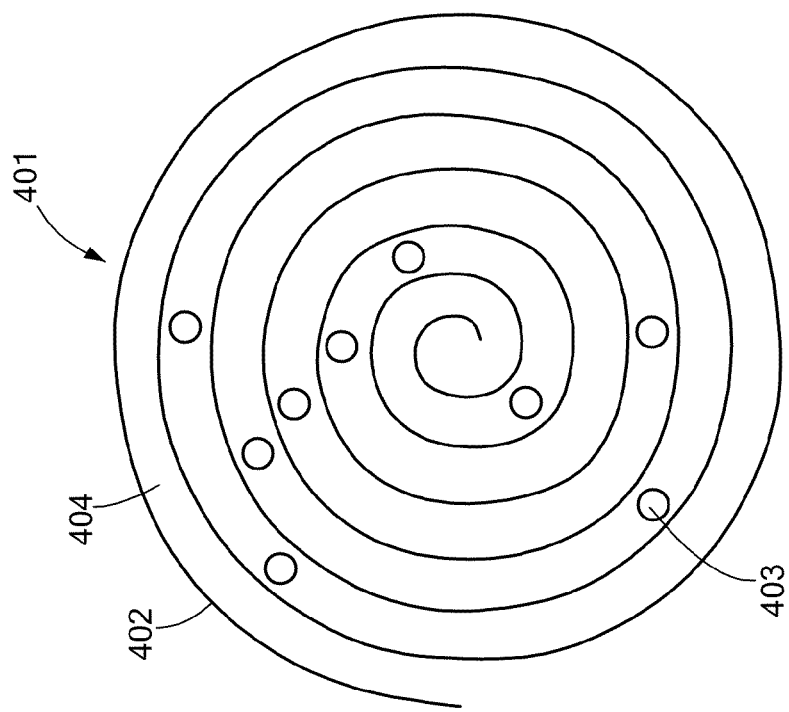

FIG. 4 A-B shows embodiments of an inductive coil 401 as described above which includes an encapsulation layer 404 of soft biocompatible material covering the wire loops 402. In FIG. 4 A-B, the encapsulation layer 404 also includes ventilation openings 403 for ventilation of the underlying skin. The ventilation openings 403 may be as shown in FIG. 4A where they are a uniform size and shape. Or in other embodiments, the ventilation openings 403 may be as shown in FIG. 4B where they are different sizes. The encapsulation layer 404 may include a substance that inhibits production of cerumen (ear wax) in the ear canal 207. In some embodiments, the wire loops may 402 be concentrated as shown in the embodiment in FIG. 4B at one or more radii 405 from a central axis of the inductive coil 401.

One of skill in the art will appreciate that there are various technical, medical and surgical considerations associated with such arrangements. For example, skin thickness around the mastoid region (where transcutaneous transmission occurs in the prior art) is relatively thick and rather variable over the patient population—typically 4 to 7 mm, but with extreme cases of only 1 mm in very young children, to more than 8 or even 10 mm in some adults. By contrast, skin thickness in the ear canal 207 is relatively small (1 to 2 mm) and its variance over the patient population also is relatively small. Thus, the power transfer coefficient of an ear canal inductive coil system is higher than in a conventional mastoid region transcutaneous link system as a result of the reduced distance between the transmitter coil 205 and the receiver coil 206. Moreover, embodiments of the present invention do not use holding magnets which disadvantageously absorb and dissipate energy from the communication signal.

The associated surgical procedure will be easier and faster compared with existing methods and no bone drilling may be needed. The placement of the receiver coil 206 between the bony wall and the skin of the ear canal 207 can be performed from any surgical access from behind the outer ear 101 which is in use for the placement of hearing implants. The receiver coil 206 may be placed in a small pouch where the skin covering the ear canal 207 is surgically lifted off from the ear canal bone, with a posterior approach. The receiver coil 206 should be placed in a lateral or medial position such that the transmitter coil 205 can fit comfortably in the outer portion of the ear canal 207 without being located too close to the tympanic membrane 102. For example, the coils may be placed on the back side (posterior side) of the ear canal 207. Alternatively, coil placement on the superior (upper) or on the inferior (lower) wall of the ear canal 207 also may be workable. Coil placement on the anterior side (front side) of the ear canal 207 may be less desirable since the anterior ear canal wall is not adequately convex, and also in such a location the coils might interfere with vascular stripes and nerve supply of the ear canal 207. If the receiver coil 206 is placed more laterally in the ear canal 207, small parts of the pinna cartilage can be resected.

Though there is growth in the ear canal 207 of young children, it seems likely that a single size of the receiver coil 206 can fit all patients from very young children to adults. For the transmitter coil 205, different sizes may be needed to cover young children as well as adults. The risk of secondary atrophy of the skin between the receiver coil 206 and the transmitter coil 205 should be significantly minimized because the without holding magnets, less pressure on the skin between the coils is needed. There should not be risk of infection for the skin pouch in the ear canal 207 since the skin can be left intact through the surgical procedure. Postoperative soft packing of the ear canal 207 may be recommended to avoid hematoma of the skin pouch. Moreover, because the total volume of the implanted receiver coil 206 is smaller, less implanted material is in contact with the surrounding tissues (advantageous in case of allergic reactions).

Ear canal inductive coils would also be compatible with combined electric-acoustic stimulation (EAS) hearing systems. The transmitter coil 205 does not fill a significant amount of space in the ear canal 207 since it lies flat in conformity with the outer wall of the ear canal 207. There would be still enough space within the outer ear canal 207 to additionally place a loudspeaker or tube from an in-the-ear component of an EAS system to deliver sound to the tympanic membrane 102.

The transmitter coil 205 should be removable at night (during sleep) so that the ear canal 207 can recover from the mechanical stress of carrying the coil. The transmitter coil 205 should also be easily cleanable and should be designed to take into account the presence of cerumen (earwax) in the ear canal 207. That is, the transmitter coil 205 should be designed so it can be inserted into the external ear canal 207 without pushing earwax towards the tympanic membrane 102. For example, an innermost end of the transmitter coil 205 nearest the tympanic membrane 102 may include a sealing edge that folds back when the transmitter coil 205 is inserted into the ear canal 207. The sealing edge then may lift off slightly when taking the transmitter coil 205 out of the ear canal 207. The transmitter coil 205 may also be coated by a material which reduces the production of earwax.

Embodiments of the present invention provide a better aesthetic appearance than current systems which rely on a bulky behind-the-ear (BTE) coil arrangement. With transfer of the data and energy components of the communication signal through the ear canal 207, the transmitter coil 205 is much smaller and no longer visible, and instead, only a less obtrusive BTE sound processor 201 is visible.

Other advantages of an ear canal coil arrangement include that there no attachment magnets are needed for fixation of the transmitter coil 205 either in the implanted receiver coil 206 or in the external transmitter coil 205 placed inside the ear canal 207. This is highly beneficial in case the patient needs to undergo Magnetic Resonance Imaging (MRI). Moreover, the probability that an ear canal coil might be wiped off unintentionally (e.g. when combing the hair or when dressing or undressing) is much reduced over conventional coils placed on the side of the head. And particularly for children, the ear canal coil arrangement is better protected and less sensitive for destructive forces such as accidental impact.

In addition, the receiver stimulator 202 can be surgically placed closer to the outer ear 101 than in hearing implant systems with conventional inductive links located on the side of the head. In conventional hearing implant systems, the position of the receiver coil and the receiver stimulator directly attached to it is somewhat limited by the possible usable locations for the external transmitter coil. For example, the external transmitter coil cannot be located too close to the outer ear 101 since then it would collide with the BTE sound processor 111.

On the other hand, in some embodiments, in addition to the ear canal arrangement of the transmitter coil 205 and implanted receiver coil 206, it may be useful to also include a secondary receiver coil, for example, as conventionally in the receiver stimulator 202, which is arranged to cooperate with a corresponding secondary external transmitter coil, for example, as conventionally in the BTE sound processor 111. This alternative conventional BTE coil arrangement may provide a secondary insurance channel in the event of problems or failure with the in the ear canal coils, or at any time that the patient user finds that the BTE coils are more suitable for use.

Some embodiments may also include an ear canal microphone attached to the transmitter coil 205 for sensing sound present in the ear canal 207. Since there is already the coupling lead 203 between the BTE processor 201 and the transmitter coil 205, this may be also exploited to add an ear canal microphone, either by attaching the microphone and the connecting cables to the connection wires for the transmitter coil 205, or by using the same cables and modulating the signals.

An ear canal transmitter coil 205 and implanted receiver coil 206 can be significantly smaller than the coils in conventional inductive link systems. While conventional inductive link coils have a diameter of about 25 to 30 mm, the coils for an ear canal inductive signal and energy transfer link may be much smaller, e.g., 10 to 15 mm. This is possible because of the reduced distance between the primary transmitter coil 205 and the secondary receiver coil 206, and because there is no attachment magnet that absorbs energy from the alternating magnetic fields associated with transmission of the communication signal. With reduced coil size, the voltages induced from external alternating magnetic fields (as during MRI) generally are also reduced.

If the implanted receiver coil 206 bends around more than about half of the circumference of the external ear canal 207, it will be very sensitive to the non-homogeneous magnetic field from the transmitter coil 205, but less sensitive to homogeneous alternating magnetic fields coming from more distant coils such as MRI scanners. Furthermore, due to the curved plane arrangement of the transmitter coil 205 and receiver coil 206, good inductive coupling can be achieved with relatively low loss of magnetic flux. This is even the case with the air coils that used and described above, and there is no need to use magnetic cores or ferrites to realize acceptable inductive coupling.

The RF pulses in MRI scanners in bore systems (with horizontal orientation) are present in x- and y-direction (i.e. within an axial plane). And coils of conventional BTE inductive links are oriented about a generally sagittal plane, but coils placed in the ear canal are oriented in a mainly axial or coronal plane. As a result, the RF pulses from an MRI scanner induce lower voltages in the secondary receiver coil of an ear canal inductive link system than in the secondary receiver coil of a conventional inductive link system.

Figure 5:
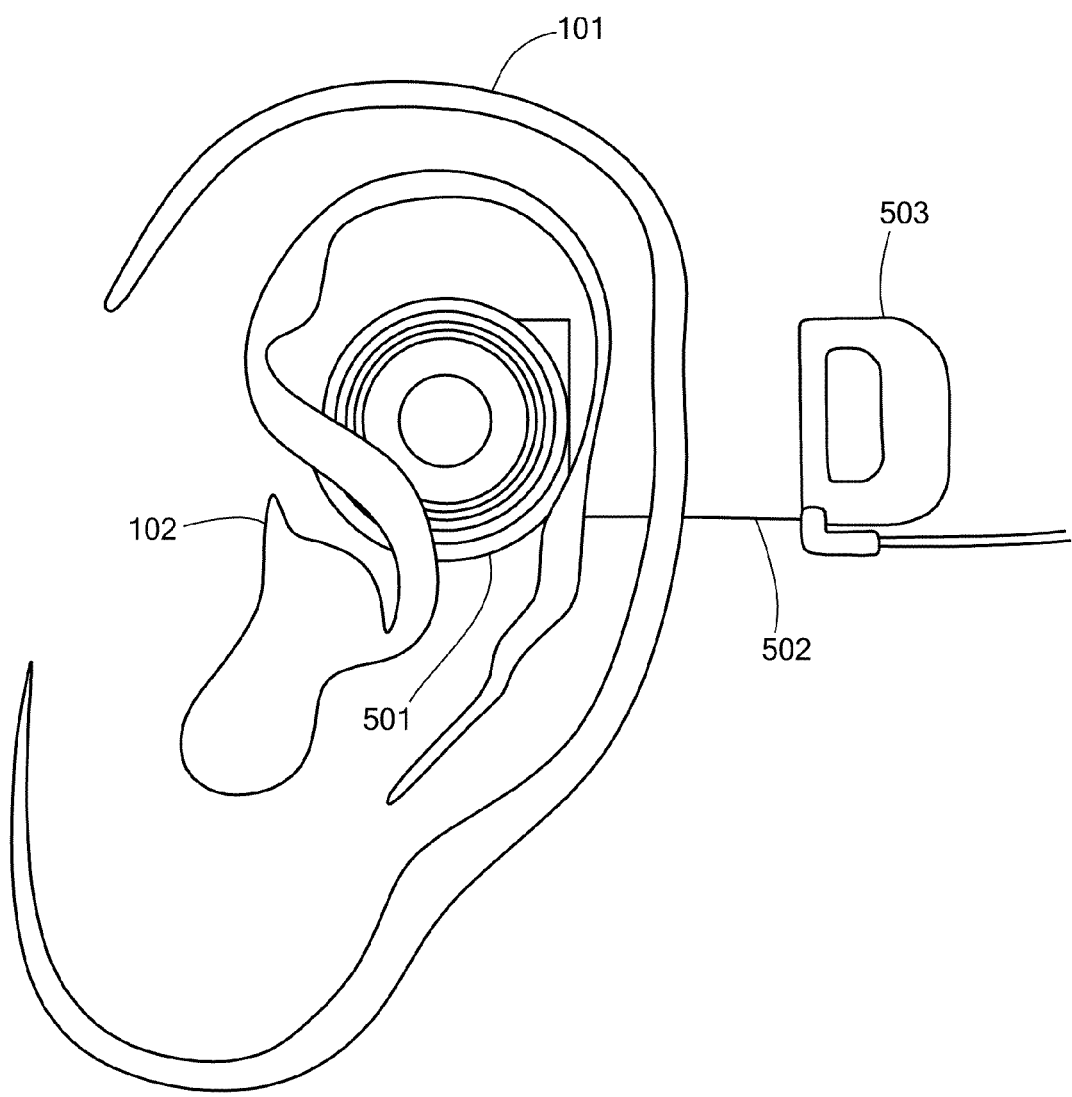
FIG. 5 shows an embodiment where the receiver coil is implanted on the backside of the pinna cartilage structure between bone and pinna.

FIG. 5 shows an embodiment where the receiver coil 501 is implanted on the backside of the cartilage structure of the outer ear 101 (the pinna) to lie in a plane under the pinna and atop and parallel to the underlying skull bone. For example, in one typical such embodiment, the implanted receiver coil 501 has a diameter of ~10 mm. A corresponding external transmitter coil can be integrated into an individually fitted ear piece which is placed in outer ear 101. The receiver coil 501 may be coupled by a connecting lead 502 to an implanted stimulator 503. The connecting lead 502 should be highly flexible to avoid open circuits, e.g. by using stranded gold wires incorporating carbon filaments. The receiver coil 501 can be fixed to the cartilage structure of the outer ear 101, for example with a few sutures at the outer circumference of the receiver coil 501. Such an embodiment leaves the ear canal unobstructed, an advantage which especially helpful for potential candidates for hybrid electric-acoustic systems (EAS).

Embodiments of the invention also include implantable devices and systems having an inductive coil arrangement as discussed above. Although various exemplary embodiments of the invention have been disclosed, it should be apparent to those skilled in the art that various changes and modifications can be made which will achieve some of the advantages of the invention without departing from the true scope of the invention.

What is claimed is:

1. An inductive coil arrangement for an ear canal of a recipient patient, the ear canal having an outer wall defining a generally cylindrical shape around a central ear canal axis, the inductive coil arrangement comprising:
   an inner transmitter coil for insertion into the ear canal, the transmitter coil having a plurality of transmission wire loops having a radial loop center, wherein the transmission wire loops and their radial loop center lie along a curve around the central ear canal axis conformal to the outer wall of the ear canal for transmitting a communication signal through the skin of the outer wall of the ear canal; and
   an outer receiver coil for implantation under the skin of the outer wall of the ear canal, the receiver coil having a plurality of receiver wire loops having a radial loop center, wherein the receiver wire loops and their radial loop center lie along a curve around the central ear canal axis substantially parallel to the transmitter coil for receiving the communication signal from the transmitter coil.

2. An inductive coil arrangement according to claim 1, wherein the coils and their radial loop centers curve in a C-shape partially along the circumference of the ear canal around the ear canal axis.

3. An inductive coil arrangement according to claim 2, wherein the coils and their radial loop centers curve substantially completely along the circumference of the ear canal around the ear canal axis.

4. An inductive coil arrangement according to claim 1, wherein an innermost end of the transmitter coil nearest the tympanic membrane includes a sealing edge that folds back when the transmitter coil is inserted into the ear canal.

5. An inductive coil arrangement according to claim 1, wherein the transmitter coil includes a helical ridge for promoting a screwing insertion movement when the transmitter coil is inserted into the ear canal.

6. An inductive coil arrangement according to claim 1, wherein the coils are air coils without magnetic cores.

7. An inductive coil arrangement according to claim 1, further comprising:
   an encapsulation layer of biocompatible material covering at least one of the coils.

8. An inductive coil arrangement according to claim 7, wherein the transmitter coil includes an encapsulation layer that inhibits production of cerumen.

9. An inductive coil arrangement according to claim 7, wherein the transmitter coil includes an encapsulation layer having a plurality of ventilation openings.

10. An inductive coil arrangement according to claim 9, wherein the ventilation openings have a uniform size and shape.

11. An inductive coil arrangement according to claim 9, wherein the ventilation openings have different sizes.

12. An inductive coil arrangement according to claim 1, further comprising:
   an ear canal microphone attached to the inner transmitter coil for sensing sound present in the ear canal.

13. An inductive coil arrangement according to claim 1, further comprising:
   a secondary external transmitter coil for positioning over the skin behind the ear of the patient to transmit a communication signal through the skin; and
   a secondary receiver coil for implantation under the skin behind the ear of the patient to receive the communication signal from the secondary external transmitter coil.

14. An implantable medical system including an inductive coil arrangement according to any of claims 1-11, 12 and 13.

* * * * *